US006979423B2

(12) United States Patent
Moll (10) Patent No.: US 6,979,423 B2
(45) Date of Patent: Dec. 27, 2005

(54) CARDIOPULMONARY BYPASS DEVICE AND METHOD (75) Inventor: Frederic H. Moll, Woodside, CA (US)

(73) Assignee: Intuitive Surgical, Sunnyvale, CA (US)

( * ) Notice: Subject to any disclaimer, the term of this patent is extended or adjusted under 35 U.S.C. 154(b) by 134 days.

(21) Appl. No.: 10/374,623

(22) Filed: Feb. 24, 2003

(65) Prior Publication Data
US 2003/0129084 A1 Jul. 10, 2003

Related U.S. Application Data (62) Division of application No. 09/443,170, filed on Nov. 19, 1999, now Pat. No. 6,554,790.

(60) Provisional application No. 60/109,325, filed on Nov. 20, 1998.

(51) Int. Cl.[7] .......................... A61M 1/14; A61M 37/00
(52) U.S. Cl. .................... 422/45; 422/44; 604/6.14; 604/4.01; 604/6.16; 128/DIG. 3; 128/907
(58) Field of Search ............................. 604/4.01, 5.01, 604/6.01, 6.09, 6.11, 6.13–6.16, 8, 173–6, 604/27–28, 523, 264, 272, 275, 164.01–164.02, 604/164.09, 164.1–164.11, 164.04, 164.06, 604/164.07, 166.01, 167.06, 158, 533–538, 604/170.01–170.03, 506–7, 17, 284, 48; 623/3.1, 3.26; 128/DIG. 3, 898; 261/DIG. 28; 606/167, 194, 184–189

(56) References Cited

U.S. PATENT DOCUMENTS 4,452,600 A * 6/1984 Schachar ..................... 604/521
4,712,551 A    12/1987 Rayhanabad
4,979,937 A    12/1990 Khorasani
5,190,528 A     3/1993 Fonger et al.
5,354,279 A    10/1994 Hofling
5,458,574 A    10/1995 Machold et al.
5,466,216 A    11/1995 Brown et al.

(Continued)

OTHER PUBLICATIONS

Neisius et al., "Robotic manipulator for endoscopic handling of surgical effectors and cameras", Proceedings of the First International Symposium on Medical Robotics and COmputer Assisted Surgery, vol. 2, Workshop (Part I & II)-Session VI, pp. 169-175.

(Continued)

Primary Examiner—Patricia Bianco
(74) Attorney, Agent, or Firm—Townsend&Townsend (57) ABSTRACT A method and system for performing a cardiopulmonary bypass procedure are provided. The method includes accessing a source of blood in a patient body from which source the blood is to be passed through a cardiopulmonary bypass machine, drawing blood from the source through the cardiopulmonary bypass machine and introducing the blood into an aortic artery of the patient body through a plurality of separate passages, after the blood has been passed through the cardiopulmonary bypass machine. The system includes a cardiopulmonary bypass machine, a tubular member coupled to an outlet port of the cardiopulmonary bypass machine and a plurality of separate needle members connected in fluid flow communication with the tubular member, the needle members being arranged to be connected in fluid flow communication with an aortic artery, during a cardiopulmonary bypass procedure.

20 Claims, 9 Drawing Sheets

U.S. PATENT DOCUMENTS 5,484,399 A * 1/1996 DiResta et al. ............... 604/21
5,693,029 A 12/1997 Leonhardt
5,695,457 A 12/1997 St. Goar et al.
5,868,703 A 2/1999 Bertolero et al.
5,957,879 A * 9/1999 Roberts et al. ............ 604/6.06
6,315,751 B1 11/2001 Cosgrove et al.

OTHER PUBLICATIONS

Thring, "Robotics and telechirs: Manipulators with memory; remote manipulators; machine limbs for the handicapped", (1993) M.W. Thring/Ellis Horward Ltd., pp. 9-11, 122-131, 194-195, 235-257, 274-279.

* cited by examiner

CARDIOPULMONARY BYPASS DEVICE AND METHOD

CROSS-REFERENCES TO RELATED APPLICATIONS

This application is a divisional of and claims the benefit of priority from U.S. patent application Ser. No. 09/443,170, filed Nov. 19, 1999, now U.S. Pat. No. 6,554,790 which claims priority from U.S. Provisional Patent Application No. 60/109,325, filed Nov. 20, 1998, the full disclosures of which are incorporated herein by reference.

BACKGROUND OF THE INVENTION

1. Field of the Invention

This invention relates to the field of heart surgery. In particular, this invention provides a cardiopulmonary bypass device and method for returning oxygenated blood to the aorta artery, after the blood has been drawn from, for example, the vena cava veins or right atrium of a heart. The cardiopulmonary bypass device and method of the invention can advantageously be used in cardiopulmonary bypass performed during minimal invasive cardiovascular surgery with cardioplegia.

2. Description of the Prior Art

Cardiac surgery relates to surgical procedures performed on a patient's heart. To perform such cardiac procedures, the heart is sometimes stopped so that the desired surgical procedure can be performed on a generally stationary heart. Such stopping of the heart is often referred to as cardioplegia. To maintain blood circulation through a patient body while the heart is stopped, a cardiopulmonary bypass is often employed. Traditionally, in the case of open heart surgery, the chest is opened using a median sternotomy to gain access to the heart. In open heart surgery, access to, for example, the aorta, for cross clamping purposes for pulmonary bypass and/or the like, is readily provided. Before stopping the heart, an arterial cannula is typically connected in fluid flow communication with the aorta artery and a venous cannula is typically connected in fluid flow communication with the superior and inferior vena cava veins. The arterial cannula and the venous cannulas typically define apertures of about 0.5 inch in diameter. The cannulae are typically connected to a cardiopulmonary bypass (CPB) system so as to perform cardiopulmonary bypass. In cardiovascular bypass, blood is drawn from the vena cava veins of a patient undergoing coronary surgery. Thereafter, the blood is passed through a venous reservoir and through an oxygenator or artificial lung where it is oxygenated. A major portion of this oxygenated blood is typically filtered and returned to the patient's aorta artery for circulation throughout the body. Thus, the CPB system typically takes over the functions of the heart and the lungs of the patient by oxygenating and pumping the blood through the patient body while the patient's heart is bypassed and stopped.

Once the CPB system is operatively connected to the patient and brought into operation, the ascending aorta artery is typically cross clamped to isolate the coronary arteries from the rest of the arterial system. Thereafter, cardiac arrest is induced by typically injecting 500 to 1000 cc of cardioplegic solution into an aortic root using a needle or cannula which pierces the wall of the ascending aorta artery upstream of the cross clamp. Cardioplegic solution typically comprises aqueous solutions of potassium chloride and often contains additional substances such as dextrose, glutamate, aspartate, and various other electrolytes such as $Ca^{+2}$ and $Mg^{+2}$. The punctures of the 0.5 inch diameter venous cannulae and the arterial cannula on the two vena cava veins and on the aorta artery, respectively, often require repair before the heart can be restarted. This is typically accomplished by means of suturing. After such suturing, and after the heart is then restarted, the sutures need to be closely monitored so as to ensure that the punctures have been adequately repaired thereby to inhibit rupturing and internal bleeding after completion of the surgery.

Typically, the foregoing procedure does not present a large problem when open chest heart surgery is to be performed since the surgeon is provided with ready access to the vena cava veins and the aorta artery. However, it can happen that the surgical procedure is to be performed in a manner other than open surgery. Accordingly, in such a case, and where pulmonary bypass is required, ready access to the vena cava veins and the aorta artery may not be readily available. This is typically the case where, for example, the surgical procedure is to be performed in a minimally invasive surgical manner.

Minimally invasive surgery is a relatively recent and very important development in the field of surgery. Generally, minimally invasive surgical techniques use endoscopic or transluminal surgical approaches in performing surgery so as to inhibit trauma and morbidity associated with relatively more invasive surgical techniques such as the open heart surgical technique described above. Minimally invasive surgical techniques have been, and are in the process of being, developed to perform surgical procedures by means of endoscopic or transluminal techniques. It is desirable that myocardial protection and cardiopulmonary support are catered for in a minimally invasive manner to obviate the need to open the patient's chest, so as to permit the cardiac procedure to be conducted fully in a minimally invasive manner. Current methods of cardioplegia and performing cardiopulmonary bypass do not adequately meet this desire as evidenced in the following prior art U.S. patents, the full disclosures of which are fully incorporated herein by reference: U.S. Pat. No. 4,712,551 to Rayhanabad; U.S. Pat. No. 4,979,937 to Khoransani; U.S. Pat. No. 5,190,538 to Fonger et al.; U.S. Pat. No. 5,466,216 to Brown et al.; and U.S. Pat. No. 5,695,457 to St. Goar et al.

U.S. Pat. No. 4,712,551 to Rayhanabad discloses a vascular shunt having a plurality of branches. The various embodiments of the vascular shunt are depicted in FIGS. 1 and 8 of this patent.

U.S. Pat. No. 4,979,937 to Khoransani discloses a plurality of small cannulas connected to Y-connectors and to larger cannulas for providing blood flow during aortic procedures. More specifically, and as can best be seen with reference to FIGS. 1 and 2 of this patent, there is seen an intercostal and lumbar perfusion apparatus having a main member and a plurality of side members communicating with the main member via a Y-connector. The apparatus disclosed in this patent provides blood flow to distal organs and intercostals during aortic surgery.

U.S. Pat. No. 5,190,538 to Fonger et al. discloses a cannula within the left atrium of the heart for draining blood and returning it via an arterial cannula after passing through an extra-corporeal pump. The atrium of the heart is pierced by a needle assembly to enable insertion of a catheter and the cannula.

U.S. Pat. No. 5,466,216 to Brown et al. discloses a pair of cannulae, respectively, inserted into the aortic root and the coronary sinus of a heart (see FIG. 1). A system or assembly interconnects the two cannulae for delivery of blood and cardioplegic solution to the aortic root for antegrade infusion or to the coronary sinus for retrograde infusion.

U.S. Pat. No. 5,695,547 to St. Goar et al. discloses a complete cardioplegia and cardiopulmonary bypass system. The devices disclosed in this patent induce cardioplegic arrest for myocardial protection during cardiac surgery by direct perfusion of the coronary arteries using a transluminal approach from a peripheral arterial entry point.

The prior art above does not teach a method or an apparatus whereby cardiopulmonary bypass can be performed without having to repair cannula punctures in the aorta artery and the vena cava veins after termination of a cardiopulmonary bypass procedure.

It is an object of the present invention to provide a method of performing cardiovascular bypass for cardiac surgery with cardioplegia.

It is another object of the present invention to provide a method of performing cardiopulmonary bypass for minimal invasive cardiovascular surgery with cardioplegia.

It is another object of the present invention to provide a cardiopulmonary bypass system.

It is another object of this invention to provide an apparatus and method whereby cardiopulmonary bypass can be performed without having to repair punctures in the aorta after the cardiopulmonary bypass has been completed. It is a further object of the invention to provide a cardiopulmonary bypass apparatus and method which also inhibits having to repair punctures in the vena cava veins upon completion of the cardiopulmonary bypass procedure.

SUMMARY OF THE INVENTION

According to one aspect of the invention, a method of performing a cardiopulmonary bypass procedure is provided. The method includes accessing a source of blood in a patient body from which source the blood is to be passed through a cardiopulmonary bypass machine, drawing blood from the source through the cardiopulmonary bypass machine and introducing the blood into an aortic artery of the patient body through a plurality of separate passages, after the blood has been passed through the cardiopulmonary bypass machine.

According to another aspect of the invention, there is provided a cardiopulmonary bypass system comprising a cardiopulmonary bypass machine, a tubular member coupled to an outlet port of the cardiopulmonary bypass machine and a plurality of separate needle members connected in fluid flow communication with the tubular member, the needle members being arranged to be connected in fluid flow communication with an aortic artery, during a cardiopulmonary bypass procedure.

According to yet a further aspect of the invention, there is provided a method of performing cardiovascular bypass for cardiac surgery with cardioplegia, the method comprising the steps of:
  a) inserting a plurality of needle members into a right atrium of a patient's heart;
  b) flowing blood from the right atrium of the patient's heart, through the plurality of needle members, and to a cardiopulmonary bypass machine where the blood is oxygenated to produce oxygenated blood; and
  c) flowing the oxygenated blood of step (b) into an aorta artery extending from the patient's heart such that cardiovascular bypass is performed for cardiac surgery with cardioplegia.

The immediate foregoing method may additionally comprise inserting, prior to the flowing step (c), a plurality of aorta needle members into the aorta artery extending from the patient's heart. The flowing step (c) may comprise flowing oxygenated blood through the aorta needle members and into the aorta artery. Preferably, the aorta artery is occluded (e.g., such as by pinching the aorta artery) at a location between the patient's heart and the aorta needle members. In a preferred embodiment of the invention, the inserting step (a) includes inserting the needle members into a right auricle of the patient's heart. The needle members may each be dimensioned with an inside diameter such that each needle member has blood flowing therethrough at a respective volumetric flow rate. Similarly, the aorta needle members may each be dimensioned with an inside diameter such that each aorta needle member has blood flowing therethrough also at a respective volumetric flow rate. The needle members may communicate with a tubular member which preferably may be dimensioned with an internal diameter such that the blood flowing through the tubular member has a volumetric flow rate that is approximately equal to the sum of the respective volumetric flow rates of the blood flowing through the plurality of needle members. Similarly, the aorta needle members may communicate with a tubular member that may be dimensioned with an internal diameter such that the oxygenated blood flowing through the tubular member has a volumetric flow rate that is approximately equal to the respective volumetric flow rates of the oxygenated blood flowing through the plurality of aorta needle members.

According to yet another aspect of the invention, there is provided a method of performing cardiopulmonary bypass for minimal invasive cardiovascular surgery with cardioplegia, the method comprising the steps of:
  (a) providing a plurality of first needle members communicating with a first tubular member which is coupled to a cardiopulmonary bypass assembly;
  (b) providing a plurality of second needle members communicating with a second tubular member which is coupled to the cardiopulmonary bypass assembly;
  (c) providing a plurality of third needle members communicating with a third tubular member which is coupled to the cardiopulmonary bypass assembly;
  (d) inserting a plurality of first needle members into a superior vena cava vein extending to a heart of a patient;
  (e) inserting a plurality of second needle members into an inferior vena cava vein extending to the heart of the patient;
  (f) inserting the plurality of third needle members into an aorta artery extending from the heart of the patient;
  (g) occluding the superior vena cava vein at a location between the first needle members of step (d) and the heart of the patient, causing blood to flow from the superior vena cava vein, through the first needle members, and through the first tubular member to the cardiopulmonary bypass assembly where the blood is oxygenated;
  (h) occluding the inferior vena cava vein at a location between the second needle members of step (e) and the heart of the patient, causing blood to flow from the inferior vena cava vein, through the second needle members, and through the second tubular member to the cardiopulmonary bypass assembly where the blood is oxygenated;
  (i) occluding the aorta artery at a location between the third needle members of step (f) and the heart of the patient; and (j) flowing oxygenated blood from the cardiopulmonary bypass assembly, through the third tubular member, and through the third needle members and into the aorta artery such that cardiopulmonary bypass is performed for minimal invasive cardiovascular surgery with cardioplegia.

According to yet a further aspect of the invention, there is provided a cardiopulmonary bypass system comprising a cardiopulmonary bypass assembly, a first tubular member coupled to the cardiopulmonary bypass assembly and a plurality of first needle members coupled to the first tubular member, a second tubular member also coupled to the cardiopulmonary bypass assembly and a plurality of second needle members coupled to the second tubular member.

BRIEF DESCRIPTION OF THE DRAWINGS

The invention will now be described, by way of example, with reference to the accompanying diagrammatic drawings, in which.

DETAILED DESCRIPTION OF THE PREFERRED EMBODIMENTS

The invention will now be described with reference to FIGS. 1–9. In FIGS. 1–9, like reference numerals are used to designate similar parts unless otherwise stated. Although the present invention will now be described in the context of both delivering oxygen-depleted blood to a cardiopulmonary bypass machine and returning oxygenated blood from the bypass machine to the patient's circulatory system, e.g., a patient's aorta, without having to repair punctures in the various vessels or body organs to which the invention is applied, it should be understood that the invention will provide distinct advantages over the existing systems and methods for returning oxygenated blood to the patient even if another method of cannulating the patient's venous system is used as a source of blood for the bypass machine. In addition, it should be understood that the practice of this invention is not limited solely to minimally invasive procedures, but instead has application to any operation in which the surgeon desires to acquire a source of blood from, and/or deliver blood or other fluids (such as, e.g., saline or pharmaceutical-laced fluids) to a patient's body, most preferably to the patient's circulatory system.

Figure 1:
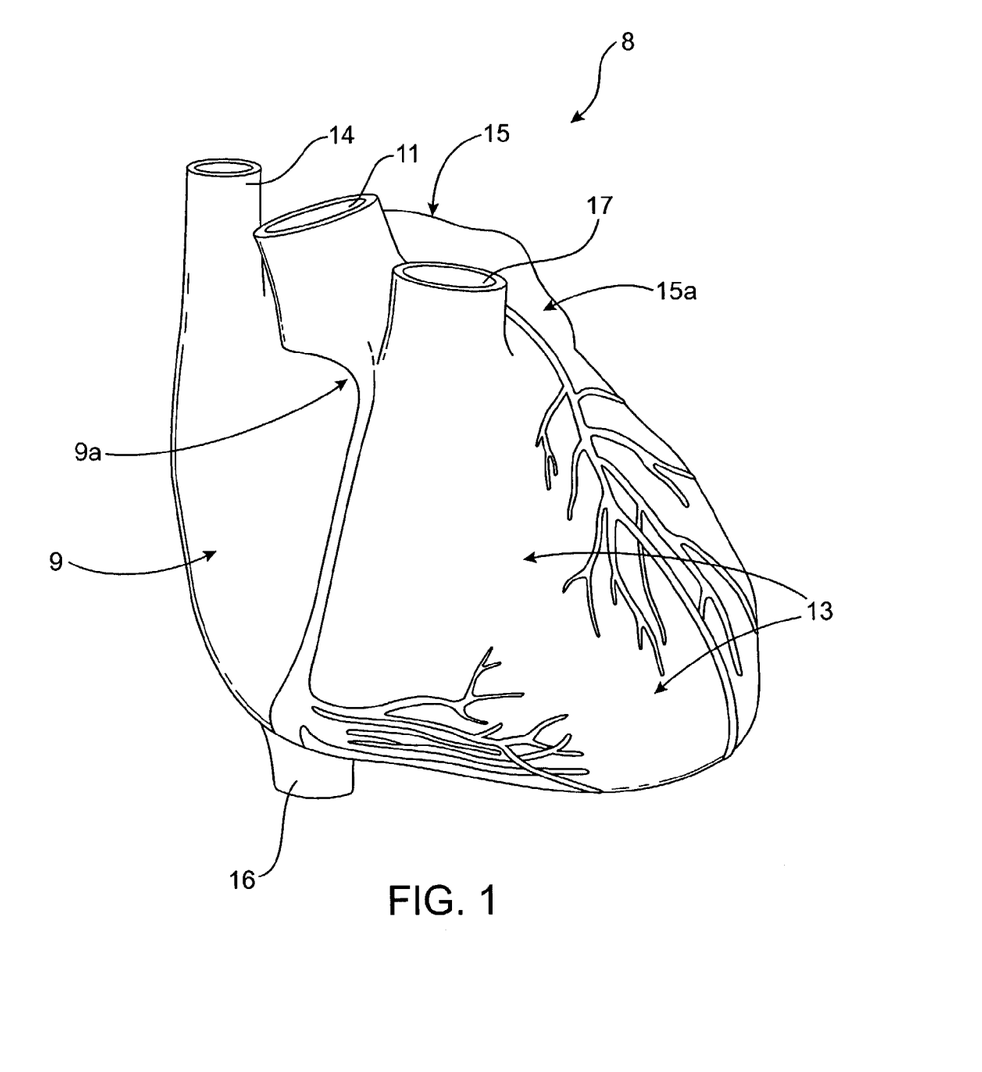
FIG. 1 shows an elevational view of a human heart.
Figure 2A:
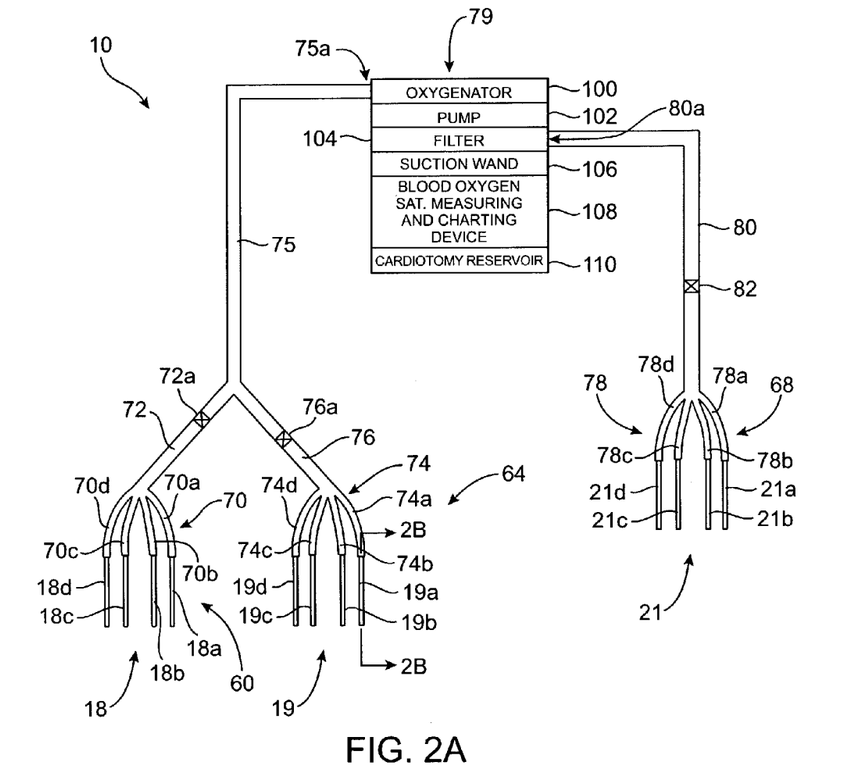
FIG. 2A shows a schematic diagram of a cardiopulmonary bypass system, in accordance with the invention, which includes needle devices also in accordance with the invention.

Referring to FIG. 1, a human heart is generally indicated by reference numeral 8. Referring to FIG. 2A, a cardiovascular bypass system in accordance with the invention, is generally indicated by reference numeral 10. The system 10 of the invention utilizes needle assemblies to access the superior and inferior vena cava veins and aorta artery respectively so as to perform cardiopulmonary bypass.

Referring again to FIG. 1, the superior vena cava vein is indicated by reference numeral 14 and the inferior vena cava vein is indicated by reference numeral 16. The veins 14, 16 are connected in fluid flow communication with the heart 8. The superior vena cava 14 and the inferior vena cava 16 feed blood to the heart after the blood has been circulated throughout a patient body (not shown). The right atrium of the heart 8 is shown at 9, and the right auricle is indicated at 9a. The aorta artery is indicated at 11 and is connected in fluid flow communication with the heart to feed blood from the heart into the circulation system of the patient body. The right ventricle of the heart is indicated at 13, the left atrium at 15, and the left auricle at 15a. A pulmonary trunk is indicated at 17.

The cardiovascular bypass system 10, in accordance with the invention, will now be described in greater detail with reference to FIG. 2A. The system 10 includes needle assemblies generally indicated at 60, 64, and 68, respectively. The needle assemblies 60, 64 are arranged to access and draw blood from the superior vena cava 14 and the inferior vena cava 16, respectively. The needle assembly 60 comprises a plurality of access needles 18a, 18b, 18c, 18d, generally indicated at 18, each of which is connected in fluid flow communication with a tube assembly, generally indicated at 70. The tube assembly 70 comprises tubes 70a, 70b, 70c, 70d, each of which is connected in fluid flow communication with a single tube 72. Each of the needles 18 is connected to a free end of one of the tubes of the tube assembly 70.

Needle assembly 64 includes a plurality of access needles 19a, 19b, 19c, 19d, which are generally indicated at 19. The needles at 19 are connected in fluid flow communication with a tube assembly, generally indicated at 74. The tube assembly 74 is connected in fluid flow communication with a tube 76. The tube assembly 74 includes a plurality of tube members 74a, 74b, 74c, 74d, each of which is connected in fluid flow communication with the tube 76. The needles 19 are connected in fluid flow communication with free ends of the tubes at 74.

The tubes 72, 76 are connected in fluid flow communication with a tube 75. Advantageously, back pressure, uniflow, or check valves 72a, 76a, can be provided to inhibit backflow of blood therethrough.

The needle assembly 68 is arranged to feed oxygenated blood to the aorta artery 11. Needle assembly 68 comprises a plurality of needles 21a, 21b, 21c, 21d, generally indicated by reference numeral 21, each of which is connected in fluid flow communication with a tube assembly 78. The tube assembly 78 includes separate tubes 78a, 78b, 78c, 78d, each of which is connected in fluid flow communication with a common tube 80. Conveniently, a backpressure valve 82 can be provided to inhibit back flow of oxygenated blood.

The tubes 75, 80 are connected in fluid flow communication with a cardiovascular bypass machine, or assembly, generally indicated at 79. The cardiovascular bypass assembly 79 comprises an oxygenator 100, a pump 102, an arterial filter 104, a suction wand 106, a blood oxygen saturation measuring and charting device 108, and a cardiotomy reservoir 110. It further comprises an inlet 75a to which the tube 75 is connected in fluid flow communication and an outlet 80a to which the tube 80 is connected in fluid flow communication.

Figure 2B:
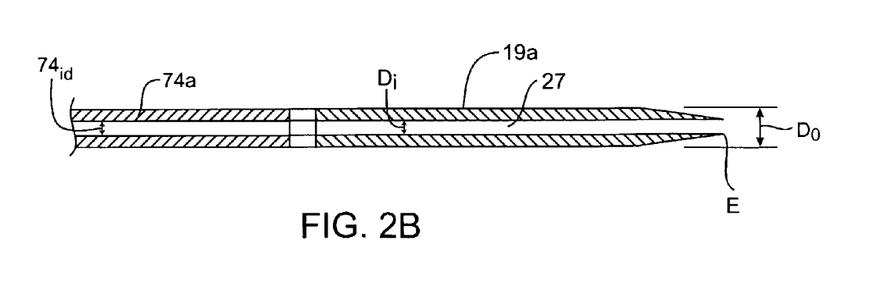
FIG. 2B shows, at an enlarged scale, a sectional view taken along arrows 2B—2B in FIG. 2A.
Figure 3:
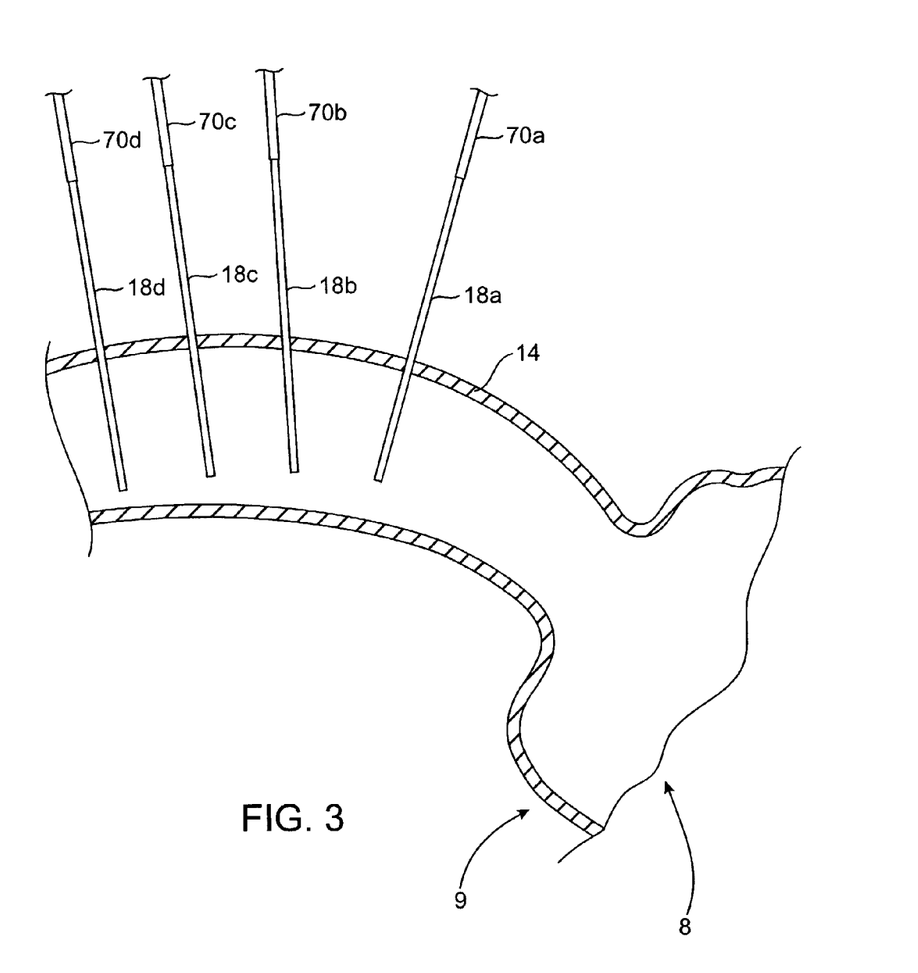
FIG. 3 shows, at an enlarged scale, a sectional view of a superior vena cava vein in fluid flow communication with a human heart of a patient, and further shows a plurality of needle members extending into the superior vena cava vein, in accordance with one aspect of the invention, such that blood can be drawn from the superior vena cava vein through the needle members during cardiopulmonary bypass.
Figure 4:
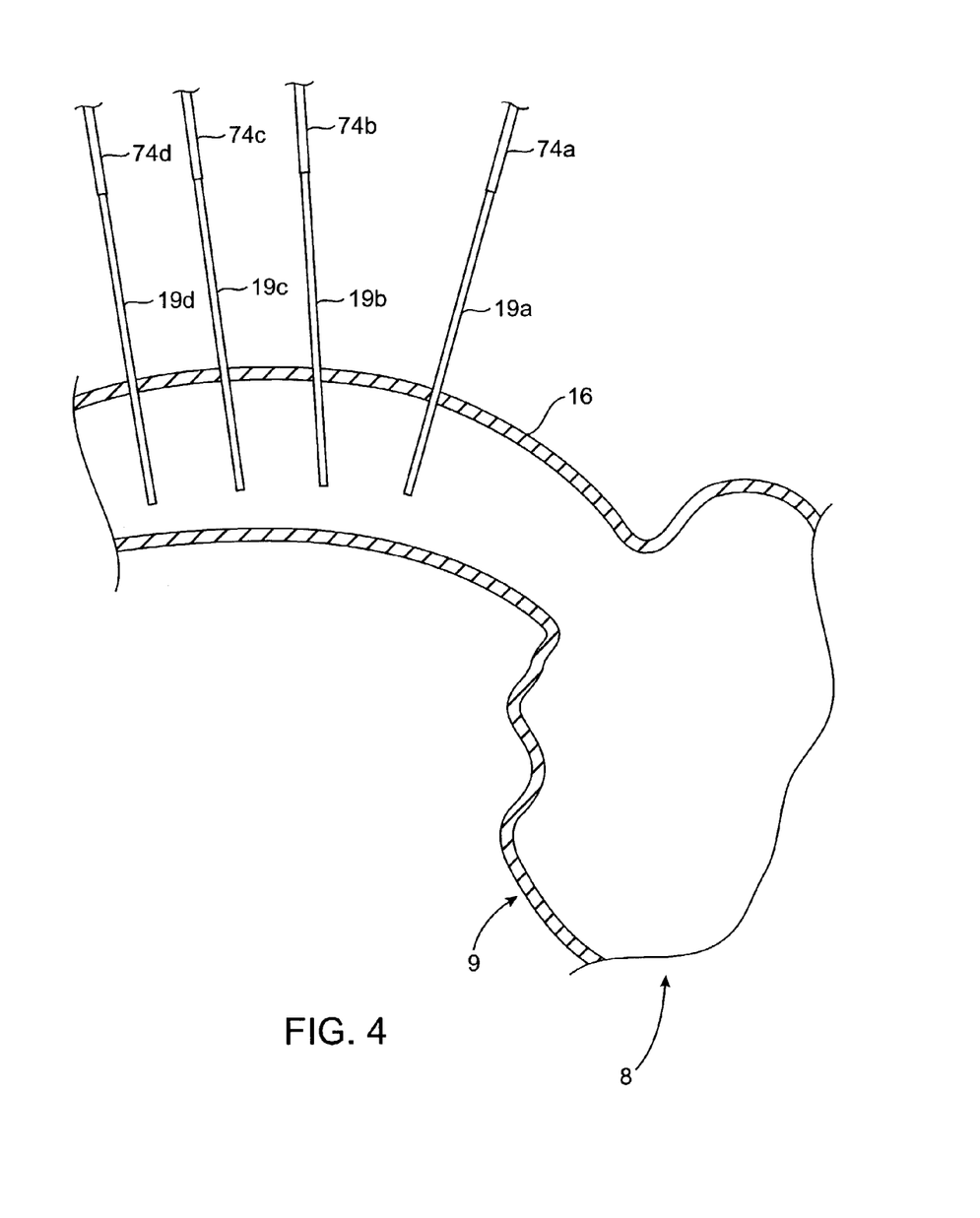
FIG. 4 shows, at an enlarged scale, a sectional view of an inferior vena cava vein in fluid flow communication with a human heart of a patient, and further shows a plurality of needle members extending into the inferior vena cava vein, in accordance with another aspect of the invention, such that blood can be drawn from the inferior vena cava vein during cardiopulmonary bypass in accordance with the invention.

Referring to FIG. 2B of the drawings, each of the needles 18, 19, 21 is typically in the form of a slender surgical needle having a sharp point or end for piercing tissue. The needles 18, 19, 21 can be made of any appropriate material, such as steel, stainless steel, or the like. Each of the needles 18, 19, 21 typically has an outer diameter $D_o$ of less than about 0.4 inches. Preferably, the needles have an outer diameter $D_o$ of less than 0.36 inches. Advantageously, each of the needles 18, 19, 21 may have an outer diameter $D_o$ falling in the range between about 0.3 inches or less.

The outer diameters $D_o$ of the needles 18, 19, 21 are typically sufficiently small so that when the needles are used to puncture the vena cava veins and the aorta artery respectively, to perform cardiopulmonary bypass in accordance with the invention, the punctures are of a size such that when the needles are withdrawn from the vena cava veins and the aorta artery, the punctures do not need to be repaired, e.g., by means of suturing, or the like. In accordance with conventional cardiopulmonary bypass techniques, the arterial cannula and venous cannulae which are typically used to access the aorta and the vena cava veins, are of a size which, when used during a cardiopulmonary bypass operation, form punctures in the vena cava veins and the aorta artery, respectively, which are of a size which requires repair after the cardiopulmonary bypass operation has been completed. It has been found that when a needle having an outer diameter of greater than about 0.5 inch is used to pierce the vena cava veins or the aorta artery, then repair is typically required to seal the puncture. Such repair is typically performed by means of suturing. Each needle typically has a sharp end, as can best be seen in FIG. 2B as indicated at E with reference to needle 19a.

It will be appreciated that each of the needle groups 18, 19, 21 are shown as having four needles for illustrative purposes only. Naturally, the number of needles used can vary and may depend on the internal diameter $D_i$ of each needle, the size of the vena cava veins 14, 16 and the aorta artery 11, the blood flow rate of the patient, and the like.

Each of the tubes of the groups 70, 74, 78 preferably has an internal diameter corresponding to the internal diameter of the needle attached to the tube. Accordingly, and as can best be seen with reference to FIG. 2B, the tube 74a has an internal diameter $74_{id}$ that is generally equal to the internal diameter $D_i$ of the needle 19a. Preferably, the individual needles of the needle groups 18, 19, 21, and the individual tubes of the tube groups 70, 74, 78 are all internally dimensioned with internal diameters such that there is a generally constant, smooth volumetric flow rate (e.g., in cc/unit of time) of blood through the individual needles and their associated tubes. Tubes 72, 76 have internal diameters such that the sum of the volumetric flow rates of blood flowing through the individual tubes 70a, 70b, 70c, 70d, and individual tubes 74a, 74b, 74c, 74d, respectively, generally equal the volumetric flow rate of blood flowing through the tubes 72 and 76, respectively. Tube 75 is also internally dimensioned with an internal diameter such that the sum of the volumetric flow rates of blood flowing through tubes 72, 76 is generally equal to the volumetric flow rate of blood flowing through tube 75. Furthermore, tube 80 typically has an internal diameter such that the volumetric flow rate of blood flowing through the tube 80 is preferably about equal to the sum of the volumetric flow rates of blood flowing through the individual tubes 78a, 78b, 78c, 78d.

It will be appreciated that the number of needles 18, 19, 21 and their internal diameters $D_i$ are chosen such that there is a consistent and smooth drawing of blood from the vena cava veins 14, 16 or from the right atrium 9, and a consistent and smooth supply of oxygenated blood into the aorta artery 11, so as to inhibit trauma to the patient. Furthermore, the outside diameters $D_o$ of the needles 18, 19, 21 are chosen such that after completion of the cardiopulmonary bypass, repair to the vena cava veins and the aorta artery to seal the punctures after the needles have been withdrawn would not be required.

Figure 9:
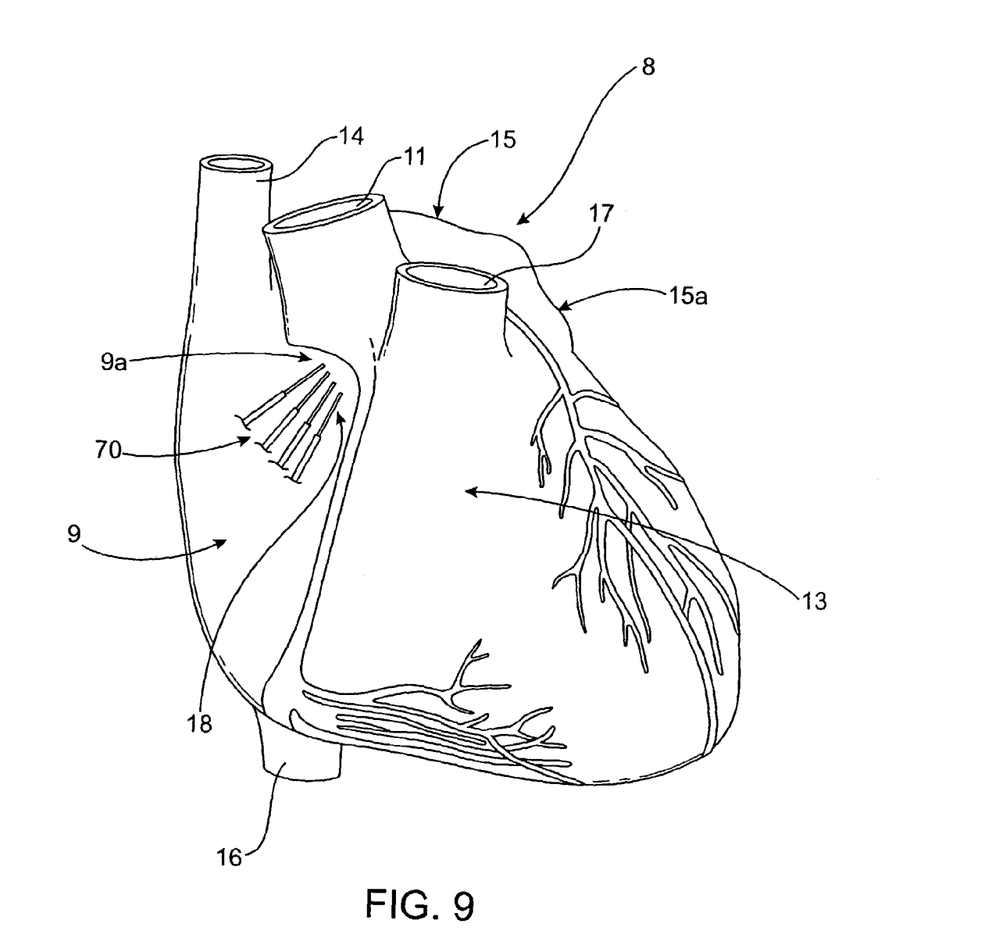
FIG. 9 corresponds to FIG. 1 and shows a plurality of needle members piercing the right auricle of the right atrium of the human heart.

In use, when a cardiopulmonary operation is performed using the system 10, the needles 18a, 18b, 18c, 18d of needle assembly 60 and the needles 19a, 19b, 19c, 19d of needle assembly 64 are introduced, preferably minimally invasively, into the superior vena cava 14 (see FIG. 3) and into the inferior vena cava 16 (see FIG. 4), respectively. With reference to FIG. 9, by way of example, the needles 18 can be inserted into the right auricle 9a of the right atrium 9 of the heart 8 instead of into the superior vena cava 14. It will be appreciated that, instead, the needles 19 can be inserted into the right auricle. Furthermore, alternatively both the needles 18, 19 in combination can be inserted into the right auricle 9a.

Figure 5:
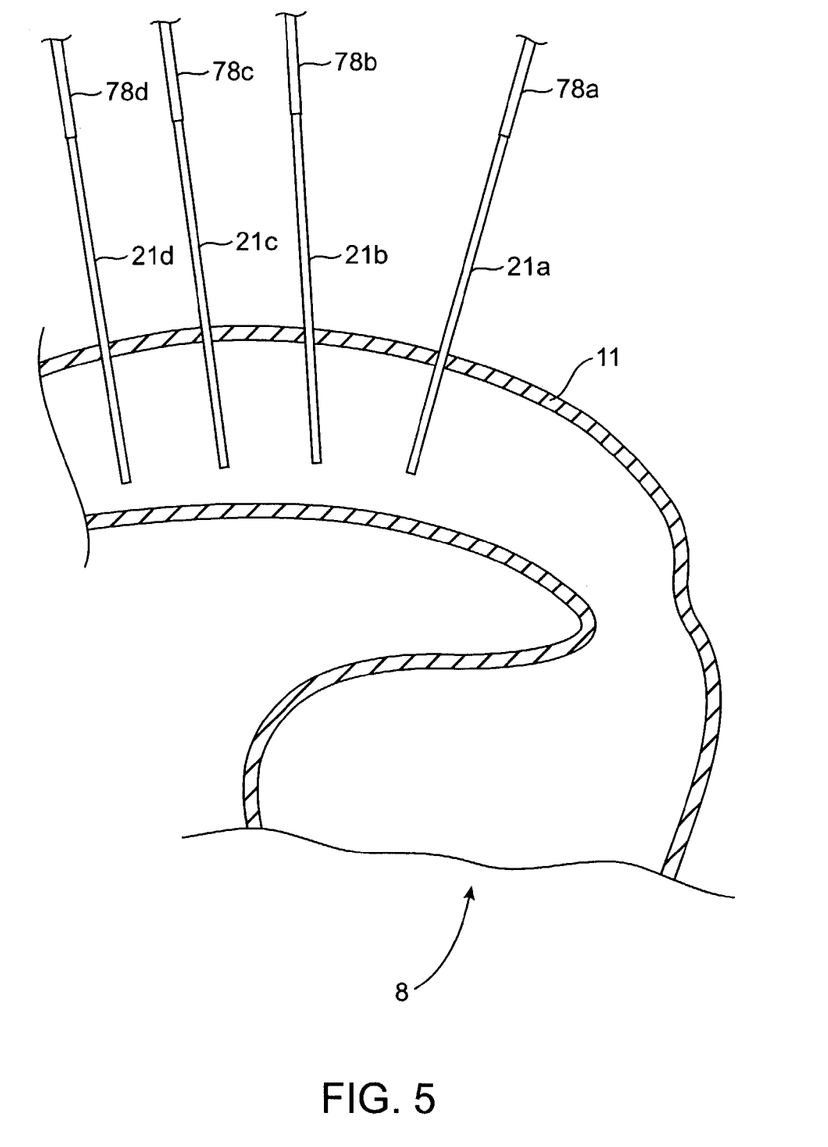
FIG. 5 shows, at an enlarged scale, a sectional view of an aorta artery in fluid flow communication with a human heart of a patient, and shows a plurality of aorta needle members extending into the aorta artery, in accordance with the invention, such that blood can be introduced into the aorta through the needle members, during cardiopulmonary bypass in accordance with the invention.
Figure 6:
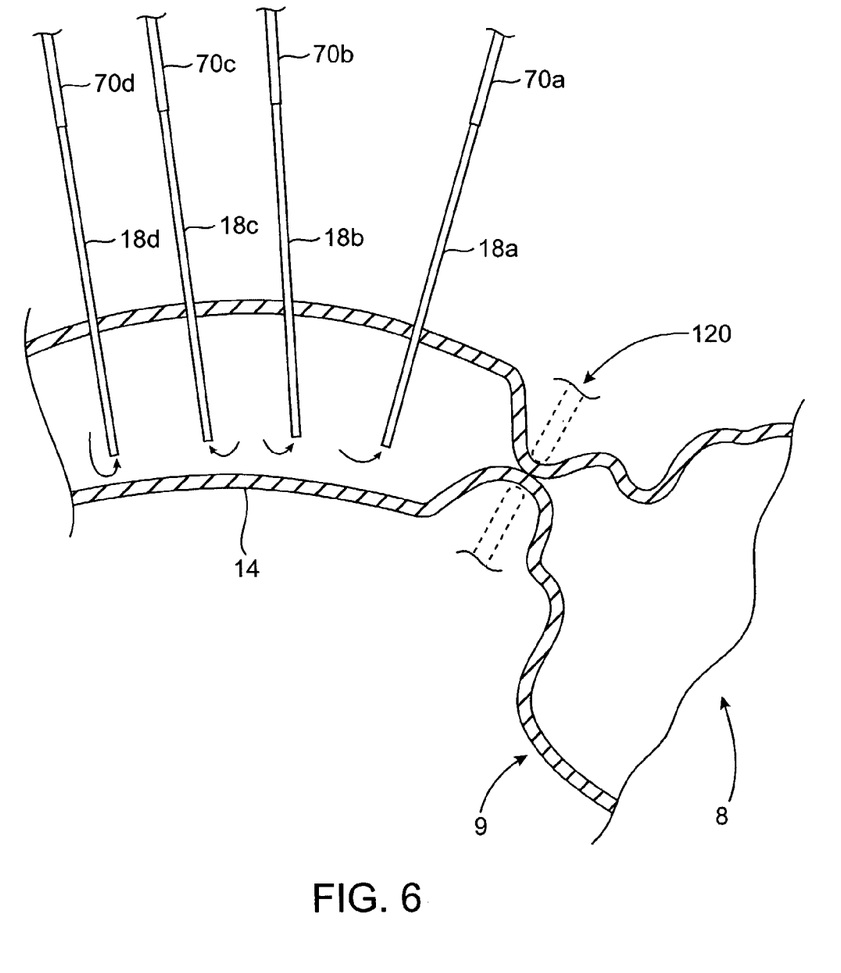
FIG. 6 corresponds to FIG. 3 and shows the superior vena cava vein being occluded by pinching it at a location between the needle members and the human heart.
Figure 7:
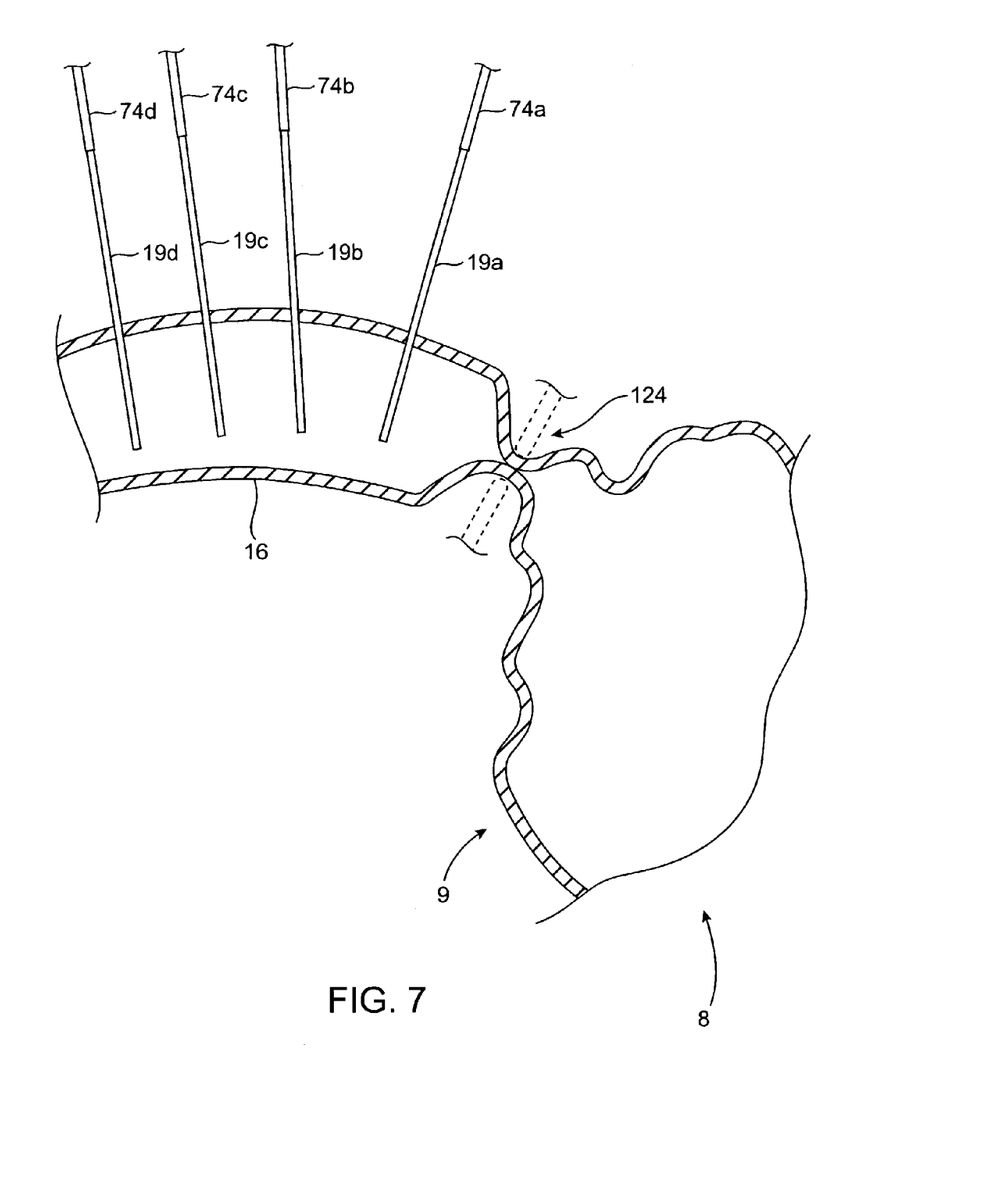
FIG. 7 corresponds to FIG. 4 and shows the inferior vena cava vein occluded by pinching at the location between the needle members and the human heart.
Figure 8:
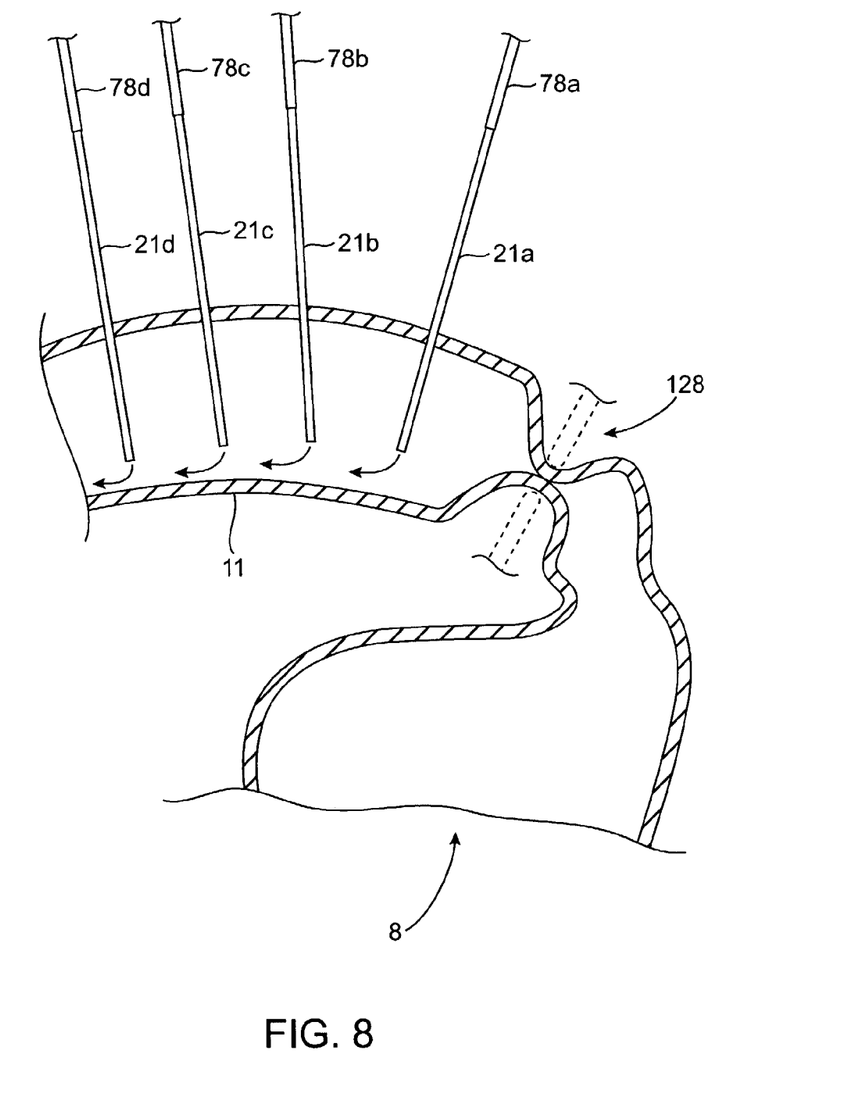
FIG. 8 corresponds to FIG. 5 and shows the aorta being occluded by pinching at the location between the aorta needle members and the human heart.

The needles 21a, 21b, 21c, 21d of the needle assembly 68 are inserted into the aorta artery 11, as can best be seen with reference to FIG. 5.

Once the respective needles have been inserted into the vena cava veins and the aorta artery, the aorta 11 is typically occluded. Such occlusion can be achieved in any appropriate manner with any appropriate apparatus or device. In one embodiment of the invention, the vena cava veins 14, 16 are respectively occluded by pinching them with pincher devices 120, 124 (see FIGS. 6 and 7) at the location on the vena cava vein 14 between the needles 18a, 18b, 18c, 18d and the heart 8, and at a location on the vena cava vein 16 between needles 19a, 19b, 19c, 19d and the heart 8, respectively. The aorta artery 11 is preferably occluded by pinching it with pincher 128 (see FIG. 8) at a location on the aorta artery 11 between needles 21a, 21b, 21c, 21d and the heart 8.

To perform the cardiopulmonary bypass, blood is then drawn from the superior vena cava 14 and the inferior vena cava 16 through the needle groups 18, 19, respectively. The blood drawn from the vena cava veins 14, 16 then flows from the needles 18, 19 through tube assembly 70 and tube assembly 74 and then into the tube 72, 76, and then into the tube 75. The blood is then fed to the oxygenator 100 by means of the tube 75, where oxygen is added to the blood and carbon dioxide is removed from the blood thereby to simulate the function of the patient's lungs.

Upon exiting the oxygenator 100, a main portion of the oxygenated blood flows to the pump 102 which pumps the blood to the arterial filter 104. The effectiveness of the oxygenator 100 is measured by an inline connection (not shown) to the blood oxygen saturation measuring and charting device 108. At the arterial filter 104, particulate matter and micro-air emboli from the oxygenated blood are removed and the filtered oxygenated blood is returned to the body of the patient through the tube 80. From the tube 80, blood flows through the tube assembly 78 and then through the needles 21 and into the aorta artery 11. In this manner, blood is circulated through the body while the heart is stopped, the cardiopulmonary system 10 simulating heart and lung function of the patient. Any blood which escapes the patient's circulatory system during the operation, is typically sucked from the chest or pleural cavity by means of a suction wand 106. The sucked blood is directed to the cardiotomy reservoir 110. In the cardiotomy reservoir 110, the blood is defoamed and filtered and fed to the oxygenator 100 to be oxygenated and returned to the patient, in the manner described above.

Instead of drawing blood from the vena cava veins as described above, and as already mentioned, blood can be withdrawn from the atrium 9 of the heart 8. As can best be seen with reference to FIG. 9, the needles of the needle group 18 can be inserted into the right auricle 9a of the right atrium 9 of the heart 8. Blood is then caused to flow through needles 18, through tube assembly 70 and tube 72, and then through tube 75 and into the cardiovascular bypass assembly 79 where the blood is oxygenated, processed and returned to the patient in accordance with the manner described above.

Accordingly, in the manner described above, a method of performing cardiovascular bypass is provided to facilitate cardiac surgery with cardioplegia. While the methods described above have been described by employing needles 18, tube assembly 70 and tube 72, it is to be appreciated that the same method may be conducted by employing needles 19, or a combination of needles 18, 19, and any tube assembly and tube(s) associated therewith. The method(s) of the present invention for performing cardiovascular bypass may be performed for the purpose of performing any type of cardiac surgery with cardioplegia. The cardiopulmonary bypass system of the invention can advantageously be used to perform cardiopulmonary bypass in accordance with the above method(s) when cardiovascular surgery is to be performed with cardioplegia, in a minimally invasive manner.

Thus, while the present invention has been described with reference to particular embodiments, a latitude of modification, various changes and substitutions are intended in the foregoing disclosure and it will be appreciated that in some instances some features of the invention will be employed without a corresponding use of other features without departing from the scope and spirit of the invention as set forth. Therefore, many modifications may be made to adapt a particular situation or material to the teachings of the invention without departing from the essential scope and spirit of the present invention. It is intended that the invention not be limited to the particular embodiments disclosed as the best mode contemplates for carrying out this invention, but that the invention will include all embodiments and equivalents falling within the scope of the appended claims.

What is claimed is:

1. A cardiopulmonary bypass system comprising:
   a cardiopulmonary bypass machine;
   an outlet tubular member coupled to an outlet port of the cardiopulmonary bypass machine; and
   a plurality of separate outlet needle members connected in fluid flow communication with the outlet tubular member, the outlet needle members being arranged to be connected in fluid flow communication with an aortic artery, during a cardiopulmonary bypass procedure.

2. A cardiopulmonary bypass system as claimed in claim 1, which further comprises an inlet tubular member coupled to an inlet port of the cardiopulmonary bypass machine and a plurality of separate inlet access needle members connected in fluid flow communication with the inlet tubular member, the inlet access needle members being arranged to be connected in fluid flow communication with a source of blood during a cardiopulmonary bypass procedure.

3. A cardiopulmonary bypass system as claimed in claim 2, which further comprises at least two tubular members branches connected in fluid flow communication with the inlet tubular member, each tubular member branch having one or more of the access needle members connected in fluid flow communication therewith.

4. A cardiopulmonary bypass system as claimed in claim 2, wherein the inlet tubular member is configured so as to have blood flowing therethrough at a first volumetric flow rate, and the plurality of separate inlet access needle members is configured so as to have the blood flowing therethrough at a second volumetric flow rate, such that the first volumetric flow rate is approximately equal to the second volumetric flow rate.

5. A cardiopulmonary bypass system as claimed in claim 2, wherein the inlet tubular member includes at least one of a back pressure valve, a uniflow valve, and a check valve.

6. A cardiopulmonary bypass system as claimed in claim 2, wherein each of the plurality of separate inlet needle member is configured to have an outer diameter of equal to or less than about 0.50 inches.

7. A carchopulmoflaJy bypass system as claimed in claim 2, wherein individual of the plurality of separate inlet needle members is configured to have an outer diameter of less than about 0.36 inches.

8. A cardiopulmonary bypass system as claimed in claim 2, wherein individual of the plurality of separate inlet needle members is configured to have an outer diameter of less than about 0.30 inches.

9. A cardiopulmonary bypass system as claimed in claim 1, wherein the outlet needle members have sharp ends for piercing a wall of the aortic artery to establish fluid flow communication therewith.

10. A cardiopulmonary bypass system as claimed in claim 1, wherein the outlet tubular member is configured so as to have fluid flowing therethrough at a first volumetric flow rate, and the plurality of separate outer needle members is configured so as to have the fluid flowing therethough at a second volumetric flow rate, such that the first volumetric flow rate is approximately equal to the second volumetric flow rate.

11. A cardiopulmonary bypass system as claimed in claim 1, wherein the outlet tubular member includes at least one of a back pressure valve, a uniflow valve, and a check valve.

12. A cardiopulmonary bypass system as claimed in claim 1, wherein each of the plurality of separate outer needle members is configured so as to have an outer diameter of equal to or less than about 0.50 inches.

13. A cardiopulmonary bypass system as claimed in claim 1, wherein individual of the plurality of separate outer needle members is configured so as to have an outer diameter of less than about 0.36 inches.

14. A cardiopulmonary bypass system as claimed in claim 1, wherein individual of the plurality of separate outer needle members is configured so as to have an outer diameter of less than about 0.30 inches.

15. A cardiopulmonary bypass system comprising a cardiopulmonary bypass assembly; a first tubular member coupled to the cardiopulmonary bypass assembly; a plurality of first needle members coupled to the first tubular member; a second tubular member coupled to the cardiopulmonary bypass assembly; and a plurality of second needle members coupled to the second tubular member.

16. A cardiopulmonary bypass system as claimed in claim 15, wherein the first tubular member is configured so as to have fluid flowing therethrough at a first volumetric flow rate, and the plurality of first needle members is configured so as to have fluid flowing therethrough at a second volumetric flow rate, such that the first volumetric flow rate is approximately equal to the second volumetric flow rate.

17. A cardiopulmonary bypass system as claimed in claim 15, wherein the second tubular member is configured so as to have fluid flowing therethrough at a first volumetric flow rate, and the plurality of second needle members is configured so as to have fluid flow therethrough as a second volumetric flow rate, such that the first volumetric flow rate is approximately equal to the second volumetric flow rate.

18. A cardiopulmonary bypass system as claimed in claim 15, wherein each of the plurality of first needle members and/or each of the plurality of the second needle members is configured so as to have an outer diameter of equal to less than about 0.50 inches.

19. A cardiopulmonary bypass system as claimed in claim 15, wherein individual of the plurality of first needle members and/or individual of the plurality of the second needle members is configured so as to have an outer diameter of less than about 0.36 inches.

20. A cardiopulmonary bypass system as claimed in claim 15, wherein individual of the plurality of first needle members and/or individual of the plurality of the second needle members is configured so as to have an outer diameter of less than boat 0.30 inches.

* * * * *